US010395361B2

(12) United States Patent
Sezginer et al.

(10) Patent No.: US 10,395,361 B2
(45) Date of Patent: *Aug. 27, 2019

(54) APPARATUS AND METHODS FOR INSPECTING RETICLES

(71) Applicant: KLA-Tencor Corporation, Milpitas, CA (US)

(72) Inventors: Abdurrahman Sezginer, Monte Sereno, CA (US); Mohammad Mehdi Daneshpanah, Foster City, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 15/803,628

(22) Filed: Nov. 3, 2017

(65) Prior Publication Data

US 2018/0082415 A1 Mar. 22, 2018

Related U.S. Application Data

(63) Continuation-in-part of application No. 15/641,150, filed on Jul. 3, 2017, which is a continuation of (Continued)

(51) Int. Cl.
*G06T 7/00* (2017.01)
*G01N 21/956* (2006.01)
(Continued)

(52) U.S. Cl.
CPC .......... *G06T 7/001* (2013.01); *G01N 21/956* (2013.01); *G03F 1/84* (2013.01); *G03F 7/705* (2013.01);
(Continued)

(58) Field of Classification Search
CPC ......... G06T 7/0006; G06T 7/00; G06T 7/001; G01N 21/956
See application file for complete search history.

(56) References Cited

U.S. PATENT DOCUMENTS 5,795,688 A 8/1998 Burdorf et al.
6,578,188 B1 * 6/2003 Pang .................. G03F 1/26
716/52
(Continued)

FOREIGN PATENT DOCUMENTS

JP 2004157518 A 6/2004
JP 2005538425 A 12/2005
(Continued)

OTHER PUBLICATIONS

Sven van Haver et al, "General imaging of advanced 3D mask objects based on the fully-vectorial extended Nijboer-Zernike (ENZ) theory", 2008, Proc. SPIE 6924, Optical Microlithography XXI, 9 pages (Year: 2008).*
(Continued)

*Primary Examiner* — David F Dunphy
(74) *Attorney, Agent, or Firm* — Kwan & Olynick LLP

(57) ABSTRACT

Disclosed are methods and apparatus for qualifying a photolithographic reticle. A reticle inspection tool is used to acquire a plurality of images at different imaging configurations from each of a plurality of pattern areas of a test reticle. A reticle near field is recovered for each of the pattern areas of the test reticle based on the acquired images from each pattern area of the test reticle. The recovered reticle near field is then used to determine whether the test reticle or another reticle will likely result in unstable wafer pattern or a defective wafer.

26 Claims, 8 Drawing Sheets

Related U.S. Application Data application No. PCT/US2016/045749, filed on Aug. 5, 2016, which is a continuation of application No. 14/822,571, filed on Aug. 10, 2015, now Pat. No. 9,547,892.

(60) Provisional application No. 62/508,369, filed on May 18, 2017.

(51) Int. Cl.
*G03F 1/84* (2012.01)
*G03F 7/20* (2006.01)

(52) U.S. Cl.
CPC .............. *G01N 2021/95676* (2013.01); *G06T 2207/10144* (2013.01); *G06T 2207/10152* (2013.01); *G06T 2207/30148* (2013.01)

(56) References Cited

U.S. PATENT DOCUMENTS

| | | | |
|---|---|---|---|
| 6,902,855 B2 | 6/2005 | Peterson et al. | |
| 7,418,124 B2 | 8/2008 | Peterson | |
| 7,570,796 B2 | 8/2009 | Zafar et al. | |
| 7,646,906 B2 | 1/2010 | Saidin et al. | |
| 7,676,077 B2 | 3/2010 | Kulkarni et al. | |
| 7,703,069 B1 | 4/2010 | Liu et al. | |
| 7,769,225 B2 | 8/2010 | Kekare et al. | |
| 7,820,341 B2 | 10/2010 | Laidig et al. | |
| 7,873,204 B2 | 1/2011 | Wihl et al. | |
| 7,932,004 B1 | 4/2011 | Xiong et al. | |
| 7,995,382 B2 | 8/2011 | Tsukamoto et al. | |
| 7,995,832 B2 | 8/2011 | Xiong et al. | |
| 8,102,408 B2 | 1/2012 | Verma et al. | |
| 8,423,927 B2 | 4/2013 | Saied et al. | |
| 8,594,823 B2 | 11/2013 | Park et al. | |
| 8,938,694 B2 | 1/2015 | Liu et al. | |
| 9,478,019 B2 | 10/2016 | Sezginer et al. | |
| 9,547,892 B2 | 1/2017 | Shi et al. | |
| 2002/0019729 A1* | 2/2002 | Chang | G03F 1/26 703/6 |
| 2004/0109601 A1* | 6/2004 | Pang | G03F 1/84 382/149 |
| 2004/0179726 A1 | 9/2004 | Burdorf et al. | |
| 2005/0244728 A1* | 11/2005 | Liu | G03F 1/36 430/5 |
| 2006/0051682 A1 | 3/2006 | Hess et al. | |
| 2006/0206852 A1* | 9/2006 | Khoh | G03F 1/36 716/53 |
| 2006/0236294 A1 | 10/2006 | Saidin et al. | |
| 2006/0242619 A1* | 10/2006 | Pang | G03F 1/84 716/139 |
| 2006/0273266 A1 | 12/2006 | Preil et al. | |
| 2008/0127027 A1 | 5/2008 | Gallatin et al. | |
| 2008/0204690 A1 | 8/2008 | Berger et al. | |
| 2009/0016595 A1 | 1/2009 | Peterson et al. | |
| 2009/0297019 A1 | 12/2009 | Zafar et al. | |
| 2010/0005440 A1 | 1/2010 | Viswanathan et al. | |
| 2010/0080443 A1 | 4/2010 | Preil et al. | |
| 2010/0162197 A1 | 6/2010 | Ye et al. | |
| 2010/0169060 A1* | 7/2010 | Zhu | G03F 7/705 703/2 |
| 2010/0325761 A1* | 12/2010 | Nakata | B82Y 15/00 850/33 |
| 2011/0276935 A1 | 11/2011 | Fouquet et al. | |
| 2011/0299759 A1 | 12/2011 | Shi et al. | |
| 2012/0121160 A1 | 5/2012 | Matsuoka et al. | |
| 2013/0058558 A1 | 3/2013 | Ueno et al. | |
| 2013/0111417 A1 | 5/2013 | Hess et al. | |
| 2013/0232454 A1 | 9/2013 | Chou et al. | |
| 2013/0236083 A1 | 9/2013 | Wang et al. | |
| 2013/0283217 A1 | 10/2013 | Fujimura et al. | |
| 2014/0254913 A1 | 9/2014 | Pang | |
| 2015/0054940 A1 | 2/2015 | Shi et al. | |
| 2015/0058814 A1 | 2/2015 | Cai | |
| 2015/0186069 A1 | 7/2015 | Sharma et al. | |
| 2015/0228063 A1 | 8/2015 | Minakawa et al. | |
| 2015/0324963 A1 | 11/2015 | Sezginer et al. | |
| 2016/0012579 A1 | 1/2016 | Shi et al. | |
| 2017/0309008 A1 | 10/2017 | Shi et al. | |

FOREIGN PATENT DOCUMENTS

| | | |
|---|---|---|
| WO | 2006019919 A2 | 2/2006 |
| WO | 20131442079 A1 | 9/2013 |

OTHER PUBLICATIONS

Wong et al, "Level-Specific Lithography Optimization for 1-Gb DRAM", 2000, IEEE Transactions on Semiconductor Manufacturing, vol. 13, No. 1, 12 pages (pp. 76-87) (Year: 2000).*
International Search Report for International Application No. PCT/US2017/064327, International Filing Date Dec. 1, 2017.
"International Application Serial No. PCT/US15/29072, International Search Report dated Jul. 31, 2016".
EPO International Search Report, Application No. 16835689.7-1022/3210189 PCT/US2016045749. Dated May 7, 2018.
"U.S. Appl. No. 14/702,336, Notice of Allowance dated Jun. 23, 2016", 9 pages.
"U.S. Appl. No. 14/822,571, Notice of Allowance dated Sep. 12, 2016", 10 pages.
"Chinese Search Report", CN Search Report, App. No. 201580023431.2, dated Jun. 16, 2017, 62 Pages.
"International Application Serial No. PCT/US15/29072, International Search Report dated Jul. 31, 2015".
"International Application Serial No. PCT/US2016/045749, Search Report dated Nov. 7, 2016", 3 pgs.
Howard, William B. et al., "Production Evaluation of Automated Reticle Defect Printability Prediction Application", Mask and Lithography Conference, 23rd European, Jan. 2007, 2 pgs.
Wang, Zhuo et al., "Spatial light interference microscopy (SLIM)", Optics Express, vol. 19, No. 2, Jan. 2011, 11 pages.

* cited by examiner

APPARATUS AND METHODS FOR INSPECTING RETICLES

CROSS-REFERENCE TO RELATED APPLICATIONS

This application claims the benefit of priority of and is a Continuation-in-Part of U.S. patent application Ser. No. 15/641,150 filed 3 Jul. 2017 by Rui-fang Shi et al., which claims the benefit of priority under 35 U.S.C. § 120 of PCT Application No. PCT/US2016/045749, filed Aug. 5, 2016 by Abdurrahman Sezginer et al, which claims the benefit of priority of prior application U.S. application Ser. No. 14/822,571, filed 10 Aug. 2015, now U.S. Pat. No. 9,547,892, issued 17 Jan. 2017 by Abdurrahman Sezginer et al. This application also claims the benefit of priority of U.S. Provisional Application No. 62/508,369 filed 18 May 2017. These applications and patent are herein incorporated by reference in their entirety for all purposes.

TECHNICAL FIELD OF THE INVENTION

The invention generally relates to the field of reticle inspection. More particularly the present invention relates to pattern qualification.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. The device is fault free prior to shipment to the end users or customers.

An integrated circuit is typically fabricated from a plurality of reticles. Initially, circuit designers provide circuit pattern data, which describes a particular integrated circuit (IC) design, to a reticle production system, or reticle writer. The circuit pattern data is typically in the form of a representational layout of the physical layers of the fabricated IC device. The representational layout includes a representational layer for each physical layer of the IC device (e.g., gate oxide, polysilicon, metallization, etc.), wherein each representational layer is composed of a plurality of polygons that define a layer's patterning of the particular IC device. The reticle writer uses the circuit pattern data to write (e.g., typically, an electron beam writer or laser scanner is used to expose a reticle pattern) a plurality of reticles that will later be used to fabricate the particular IC design.

Some reticles or photomasks are in the form of an optical element containing at least transparent and opaque regions, semi-transparent and phase shifting regions, or absorber and reflective regions, which together define the pattern of coplanar features in an electronic device such as an integrated circuit. Reticles are used during photolithography to define specified regions of a semiconductor wafer for etching, ion implantation, or other fabrication processes.

After fabrication of each reticle or group of reticles, each new reticle typically is qualified for use in wafer fabrication. For example, reticle patterns need to be free of printable defects. Additionally, any wafer that is fabricated with the reticle needs to be free of defects. Thus, there is a continuing need for improved reticle and wafer inspection and qualification techniques.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of qualifying a photolithographic reticle is disclosed. An imaging tool is used to acquire a plurality of images at different illumination configurations and/or different imaging configurations from each of a plurality of pattern areas of a test reticle. A reticle near field is recovered for each of the pattern areas of the test reticle based on the acquired images from each pattern area of the test reticle. The recovered reticle near field is then used to determine whether the test reticle or another reticle will likely result in unstable wafer pattern or a defective wafer.

In one implementation, the reticle near field is directly analyzed to determine whether the test reticle or another reticle will likely result in an unstable wafer pattern or a defective wafer. In another aspect, the recovered reticle near field is used to detect defects in the test reticle or in simulated wafer images that are simulated from the recovered reticle near field, wherein defect detection includes comparing intensity and/or phase for a same die at different times, for adjacent dies, for a die and its corresponding golden die, or for a die and a corresponding die from a reticle copy with identical design to the test reticle.

In one aspect, the images are acquired at a field plane or a pupil plane. In a specific embodiment, the reticle near field is recovered without using a design database that was used to fabricate the reticle. In another aspect, the acquired images include at least three reflective/transmissive images that are acquired at different imaging conditions that are selected to result in a same reticle near field. In this aspect, the different imaging conditions include different focus settings and different pupil shapes, and the different illumination conditions include different source intensity distribution and/or polarization settings.

In an alternative implementation, the method includes (i) applying a lithography model to the reticle near field for the test reticle to simulate a plurality of test wafer images and (ii) analyzing the simulated test wafer images to determine whether the test reticle will likely result in an unstable or defective wafer. In this aspect, the lithography model is configured to simulate a photolithography process. In a further aspect, the lithography model simulates an illumination source having a different shape than an illumination shape of an inspection tool for acquiring images of the test reticle or another reticle or wafer. In another aspect, the lithography model is calibrated with images rendered from a design database for a calibration reticle. In another example, the lithography model is calibrated with images acquired from a calibration reticle. In yet a further aspect, the lithography model is applied to the reticle near field, which was recovered for the test reticle, under a plurality of different lithography process conditions, and analyzing the simulated test wafer images includes determining whether the test reticle will likely result in an unstable wafer under the different lithography process conditions by comparing portions of the simulated test images associated with different process conditions and a same reticle area.

In an alternative embodiment, the invention pertains to an inspection system for qualifying a photolithographic reticle. The system includes a light source for generating an incident beam and an illumination optics module for directing the incident beam onto a reticle. The system also includes a collection optics module for directing an output beam from each pattern area of the reticle to at least one sensor for detecting the output beam and generating an image or signal based on the output beam. The system further comprises a controller that is configured to perform operations that are similar to one or more of the above described method operations.

These and other aspects of the invention are described further below with reference to the figures.

DETAILED DESCRIPTION OF EXAMPLE EMBODIMENTS

Figure 1:
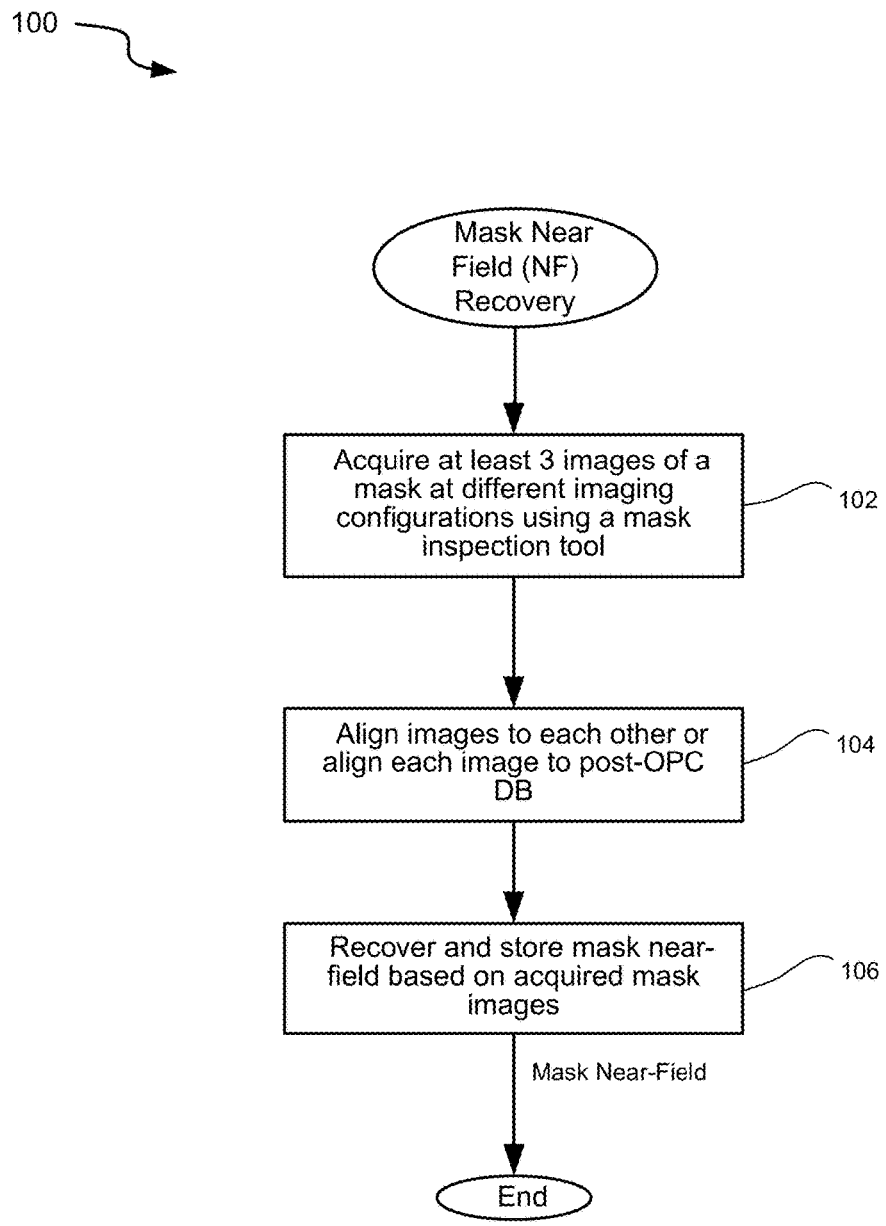
FIG. 1 is a flow chart illustrating a mask near field recovery procedure in accordance with one embodiment of the present invention.

In the following description, numerous specific details are set forth in order to provide a thorough understanding of the present invention. The present invention may be practiced without some or all of these specific details. In other instances, well known process operations or apparatus components have not been described in detail to not unnecessarily obscure the present invention. While the invention will be described in conjunction with the specific embodiments, it will be understood that it is not intended to limit the invention to the embodiments.

It would be beneficial to detect each mask's defects and otherwise characterize various aspects of the mask (e.g., pattern stability, CD, CD uniformity) prior to shipping masks to a fabrication facility, prior to fabricating wafers using such mask for fabrication, and/or for periodic requalification of such mask after such mask has been used for certain periods of time in the fabrication process.

One embodiment of the present invention includes techniques for recovering near field images of a reticle based on reticle images obtained from an inspection tool under a plurality of different imaging parameters. This reticle near field image may then be used in a number of reticle qualification applications. In one example, the reticle near field image may be input to a lithography model to predict a wafer image or various wafer pattern characteristics related to how the resulting patterns will be printed on the wafer. The predicted wafer image and/or various wafer characteristics may then be analyzed for defect detection, reticle qualification or requalification, and/or any other suitable metrology or inspection applications. The reticle near field image may also itself be analyzed for various purposes as further described herein.

The terms "reticle", "mask", and "photomask" are used herein interchangeably and generally each may include a transparent substrate, such as glass, borosilicate glass, quartz, or fused silica having a layer of opaque material formed thereon. The opaque (or substantially opaque) material may include any suitable material that completely or partially blocks photolithographic light (e.g., deep UV or extreme UV). Example materials include chrome, molybdenum silicide (MoSi), tantalum silicide, tungsten silicide, opaque MoSi on glass (OMOG), etc. A polysilicon film may also be added between the opaque layer and transparent substrate to improve adhesion. A low reflective film, such as molybdenum oxide (MoO2), tungsten oxide (W02), titanium oxide (TiO2), or chromium oxide (CrO2) may be formed over the opaque material. In a specific example, an EUV reticle may include multiple layers having alternating layers of different refractive indices with low absorption characteristics (such as molybdenum (Mo) and silicon (Si)) and an absorber material (such as a tantalum boron nitride film topped by a thin anti-reflective oxide).

The term reticle refers to different types of reticles including, but not limited to, a clear-field reticle, a dark-field reticle, a binary reticle, a phase-shift mask (PSM), an alternating PSM, an attenuated or halftone PSM, a ternary attenuated PSM, a chromeless phase lithography PSM, and chromeless phase lithography (CPL). A clear-field reticle has field or background areas that are transparent, and a dark-field reticle has field or background areas that are opaque. A binary reticle is a reticle having patterned areas that are either transparent or opaque. For example, a photomask made from a transparent fused silica blank with a pattern defined by a chrome metal adsorbing film can be used. Binary reticles are different from phase-shift masks (PSM), one type of which may include films that only partially transmit light, and these reticles may be commonly referred to as halftone or embedded phase-shift masks (EPSMs), such as ArF and KrF masks. If a phase-shifting material is placed on alternating clear spaces of a reticle, the reticle is referred to as an alternating PSM, an ALT PSM, or a Levenson PSM. One type of phase-shifting material that is applied to arbitrary layout patterns is referred to as an attenuated or halftone PSM, which may be fabricated by replacing the opaque material with a partially transmissive or "halftone" film. A ternary attenuated PSM is an attenuated PSM that includes completely opaque features as well.

The next generation lithography has ushered in the use of extreme ultra-violet radiation (EUV, wavelength 13.5 nm), which is absorbed in normal atmosphere as well as in glass. For this reason, lithography EUV processes take place under vacuum, and optical reflective lenses/mirrors are used for focusing onto the EUV photomasks, which will have reflective and absorber patterns, instead of translucent and opaque patterns.

FIG. 1 is a flow chart illustrating a mask near field recovery procedure 100 in accordance with one embodiment of the present invention. The following mask recovery process 100 may be performed for a particular reticle or set of reticles at any suitable time in a reticle's lifecycle as further described below in various use cases for the recovered mask near field. By way of examples, a mask near field may be recovered prior to fabrication of any wafers with such reticle(s), prior to commencement of high volume wafer fabrication, or during requalification of such reticle(s).

Initially, at least three images of the mask are acquired at different imaging configurations using a mask inspection tool in operation 102. Alternatively, two images may be used, but using three images has been found to work well. Acquisition with different imaging configurations may be simultaneous or sequential. The acquired images do not have to be at the field planes. By way of examples, the two or more images can be acquired at the pupil planes at which the diffraction intensity may be directly accessed.

Various suitable combinations of illumination and/or collection configurations may be utilized for acquiring the two or more images. The different imaging configurations are generally selected to provide images from which the mask near field may be calculated. Any suitable imaging or optical configurations may be selected so that the mask near field remains the same under the different operating conditions. Examples include different focus settings, different illumination shapes (e.g., different directions or patterns), different polarization for the entire illumination pupil or different parts of the illumination pupil, different apodization settings to obscure different portions of the collection beam, etc. In one embodiment, different focus settings, through focus and defocus (such as 0 focus, ±800 or ±1600 defocus, etc.), may be used to acquire the different images. In another example, different quadrants of the illumination pupil may have different polarization settings. In another example, the imaging configurations may include high resolution images, such as transmitted images (e.g., for ArF masks) with different pupil shapes and/or different focal conditions. In another embodiment, three or more reflected images with different pupil shapes and/or different focal conditions may be obtained (e.g., for EUV masks).

The reticle may be imaged at a "substantially low resolution" using a relatively low NA (e.g., less than 0.5). In contrast, a "substantially high resolution image" generally refers to an image of a reticle in which features printed on the reticle appear substantially as they are formed on the reticle (within the optical limitations of the reticle inspection system used to generate the image). A "substantially high resolution image" of a reticle is an image that is generated by imaging the physical reticle at the reticle plane with a substantially high resolution reticle inspection system (e.g., a numerical aperture (NA) of greater than 0.8). The "substantially low NA" used to generate a reticle image may be substantially the same as the NA on the reticle side that is used by an exposure/lithography system to project an image of the reticle onto a wafer, thereby transferring features of the reticle onto the wafer. In the substantially low NA image (or LNI), the reticle features may have a substantially different appearance than the actual reticle features. For example, reticle features may appear to have more rounded corners in an LNI of a feature than the actual feature that is formed on the reticle.

In general, any suitable imaging tool may be used for the mask near field recovery process. In certain embodiments described herein, the results of an initial recovery process may be later used for pattern stability or defect detection assessments with respect to the same reticle or other reticles based on additional reticle images from a particular inspection tool. For consistency in these use cases, the images of the reticle for mask near field recovery may be acquired with the detector of the reticle inspection system that will be used for subsequent inspection of the same or other reticles or acquired with a similarly configured detector of a similarly configured reticle inspection system (e.g., a different reticle inspection system of the same make and model as the reticle inspection system that will be used for inspection). In other words, the images that may be used for mask recovery may be acquired under the same optical conditions as will be used during subsequent mask inspection or qualification processes. In this manner, the interaction of the reticle with the illuminating electromagnetic waves of the inspection system may be measured as directly as possible.

In alternative embodiments, the tool used for mask near field recovery may differ from a reticle inspection system. For instance, the imaging tool may utilize the same wavelengths (e.g., wavelength 193.3nm for DUV or 13.5 nm for EUV) as the lithography system in which the reticle will be used for wafer manufacturing. In fact, any suitable electromagnetic wavelength may be used for the mask near field recovery, for example, if the purpose is defect detection.

Referring back to the illustrated example, the three or more images may then be aligned with each other or each image may be aligned to the post-OPC database in operation 104. For instance, the acquired images may be aligned via spatial-domain or frequency-domain methods. Alignment adjustments may depend on specific geometries of the imaging system being used. If different images are obtained using different collection paths, some adjustment of the images can be made to compensate for differences in optical paths.

In the imaging tool, a reticle having various patterns is illuminated by electromagnetic (EM)-waves that are incident from many directions. This incident light is diffracted from different points of the mask pattern at different electromagnetic field phases which interfere with each other differently. The near-field of the reticle is the electromagnetic field at a proximate distance of a few wavelengths from the reticle.

The collection optics generally directs a diffraction-limited portion of the light from the reticle towards a detector (or wafer) to form an image. The detector detects intensity which is the result of interference due to the mask near field, but does not detect the phase.

Although far-field intensity is obtained in the detected signals, it is desirable to recover the mask near field, which includes amplitude and phase. In the illustrated embodiment, the mask near field is recovered and stored based on such acquired mask images, as illustrated in operation 106. Multiple images (or signals) are generally used to recover the mask near field, which includes both phase and amplitude components. The near-field data may be determined by a regression technique based on the images acquired from the reticle. For example, the near-field of a selected portion of the reticle can be recovered (regressed), using a quasi-Newton or conjugate gradient technique, from its acquired optical images or intensity of images recorded at a detector plane. In addition, any other suitable regression method and/or algorithm may be used to determine the near-field data from the one or more actual images.

Mask near field recovery can generally be achieved by solving an optimization problem that seeks to minimize the difference between observed intensity images and resulting images of the assumed mask optical field. In particular, recovering the near-field of a reticle from its intensity images is an inverse problem or a regression problem. The near-field can be recovered iteratively by minimizing a cost function (e.g., energy or penalty function). The quantity that is minimized can be the sum of squared differences between the acquired images and intensity images at the detector that are calculated from the mask near-field. In other words, intensity images can be calculated from the final mask near field for various sets of optical system properties, and these calculated images will most closely match the acquired images when the mask near field is found. Various mask near field recovery methodology and system embodiments are described further in U.S. Pat. No. 9,478,019 issued 25 Oct. 2016 by Abdurrahman Sezginer et al., which patent is incorporated herein by reference in its entirety for all purposes.

In the case where multiple images are acquired under various optical conditions, the recovered near field mask m, which carries the phase and amplitude information, can be determined by the following equation:

$$m' = \operatorname{argmin} \sum_\alpha c_\alpha \sum_{x,y} \left[ I_\alpha - \sum_i \lambda_i^{(\alpha)} |m \otimes \psi_i^{(\alpha)}|^2 \right]^2 \quad \text{Equation 1}$$

In the above Equation 1, $I_\alpha$ is the measured image for imaging condition $\alpha$, $\psi_i^{(\alpha)}$ is a set of eigenvectors describing the inspection imaging system, $\lambda_i^{(\alpha)}$ is a set of corresponding eigenvalues for the imaging system, and $c_\alpha$ is a non-negative weighting factor between 0 and 1. The above equation can be solved iteratively through, for example, methods such as quasi-Newton or conjugate gradient.

Another example is the Gerchberg-Saxton algorithms in which a combination of field plane images and pupil plane diffraction orders can be utilized to solve both the amplitude and phase of the object.

In one embodiment, the mask near field may be determined based on the acquired images via a Hopkins approximation. In another embodiment, the regression does not include thin-mask approximations. For example, the near-field of the reticle is the electromagnetic field that is calculated to be present near the surface of the reticle when it is illuminated by a normally-incident plane wave. In lithography and inspection, a reticle is illuminated by plane-waves that are incident from many directions. When the direction of incidence changes, according to the Hopkins approximation, the directions of the diffraction orders change but their amplitudes and phases remain approximately unchanged. The embodiments described herein can use the Hopkins' phase approximation but do not make the so-called thin-mask or Kirchhoff approximations.

The recovery formulation can also be varied with different norms or the addition of a regularization term R, which penalizes oscillations in the near field, as follows:.

$$\hat{m} = \operatorname{argmin} \sum_\alpha c_\alpha \left[ I_\alpha - \sum_i \lambda_i^{(\alpha)} |m \otimes \psi_i^{(\alpha)}|^2 \right]^l + R(m)$$

where regularization term R, can incorporate prior information about the near field or expectations based on the physical understanding of the mask substrate/material. In addition, the norm used for image difference can be a 1-norm and adjusted based on specific needs of the optimization function.

As an interesting note, the interference of the mask electromagnetic field vectors as a result of a higher NA will be greater (than a lower NA inspection system) due to the wider range of incident angles of light and associated interfering electric field components for a higher NA.

The actual mask may vary from the intended design patterns due to the mask writing process. Obtaining the near field mask from images of the mask means that such near field mask is obtained from the actual physical mask, rather than the design database. That is, mask near field may be recovered without using the design database.

The mask near field results can then be used in various applications. In one embodiment, mask near field results can be used to predict wafer patterns using one or more models. That is, the recovered mask near field may be used to simulate lithography images. Any suitable technique may be utilized to simulate lithography images based on the mask near field images. One embodiment includes computation of the lithography image through the Partial Coherence Model:

$$I_{litho}(x; f, z) = \sum_i \lambda_i |\hat{a}(x) \otimes \psi_i^s(x; f, z)|^2 \quad \text{Equation 2}$$

where $\lambda_i$ represents the Eigen values of the lithography TCC (transfer cross coefficients); $\psi_i^s(\ )$ represents Eigen vectors (kernels) of TCC; s is the wafer stack, including film refractive indices; f is focus; and z is vertical position of the lithography plane in the resist material. The transfer cross coefficients (TCC) of Equation 2 may include vectorial propagation of the field through the lithography projector including the film stack on the wafer.

Prior to using a model for predicting wafer results, the model may be calibrated to produce as accurate results as possible. The model may be calibrated using any suitable technique. Certain embodiments of the present invention provide techniques for calibrating a lithography model based on mask near field results that are recovered from a calibration mask. In alternative embodiments, the design database is used to calibrate the model. For instance, calibration reticle images may be rendered from the design database.

A calibration reticle will typically be designed to have characteristic(s) that are substantially similar to the reticle to be inspected for defect detection or to be measured for metrology purposes. For example, the calibration reticle and the test reticle are preferably formed from substantially the same materials having substantially the same thicknesses and compositions. In addition, the two reticles may have been formed using the same processes. The two reticles may not necessarily have the same patterns printed thereon as long as the patterns on the reticles can be broken up into segments that are substantially the same (e.g., lines having similar widths, etc.). In addition, the reticle that will be inspected and the reticle that is used to acquire the images may be one and the same reticle.

Figure 2:
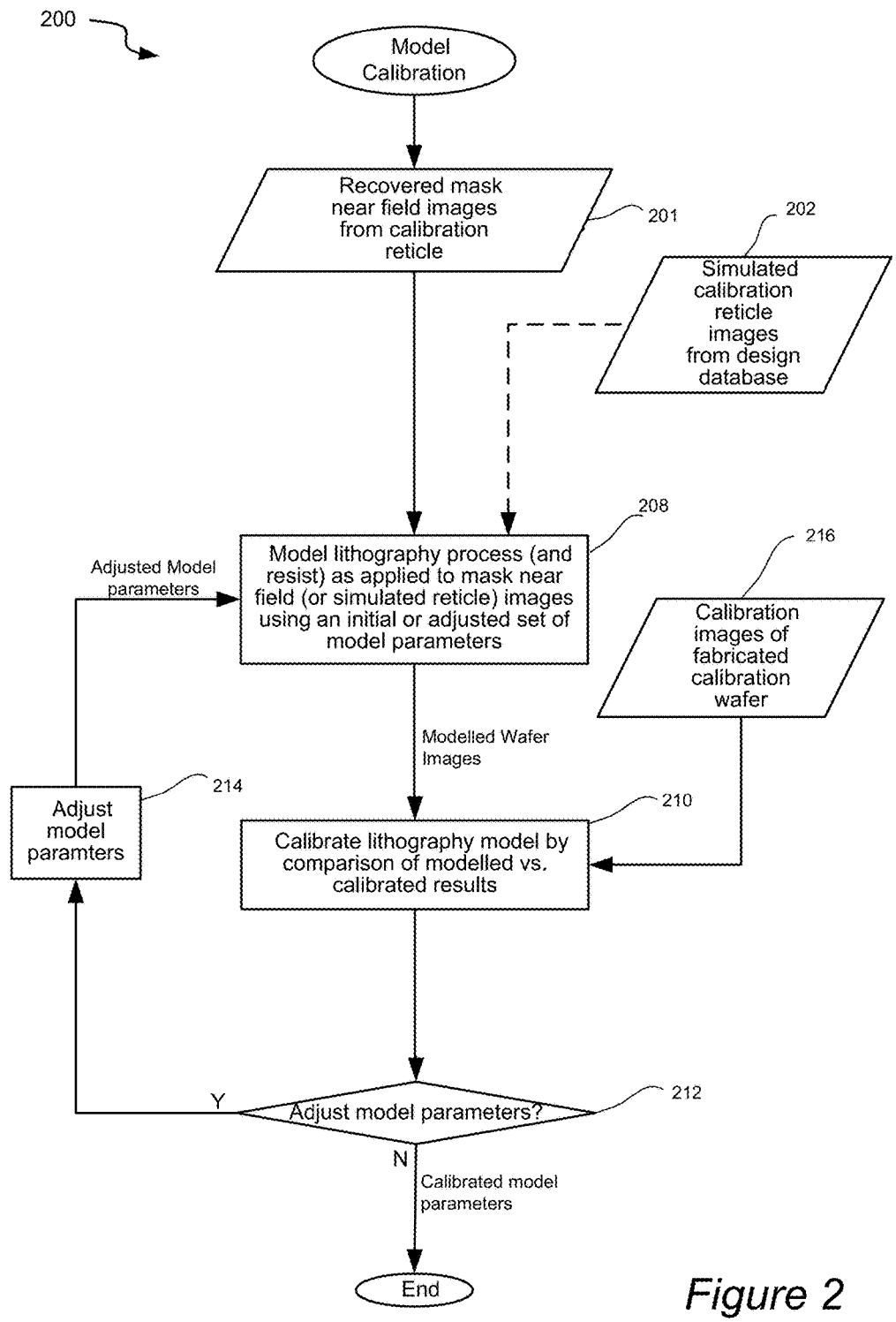
FIG. 2 is a flow chart illustrating a model calibration process in accordance with a specific implementation of the present invention.

FIG. 2 is a flow chart illustrating a model calibration process 200 in accordance with a specific implementation of the present invention. As shown, the photolithography process and photoresist can be modeled as applied to mask near field images (201) recovered from a calibration reticle using an initial set of model parameters in operation 208. Alternatively, the calibration process 200 may use simulated calibration reticle images (202) that are simulated from the design database. Reticle images may be rendered from the database by simulating the reticle fabrication and imaging processes on the design database. Any suitable model may be used to generate optical images for the features of the design database. By way of example, such simulation may include using Sum Of Coherent Systems (SOCS) or Abbe methodologies described herein. Several software packages exist that can simulate intensity images of an optical system from a known design database. One example is Dr.LiTHO developed at Fraunhofer IISB in Erlangen Germany. In the case of simulating an image from design database 202, the near field may be simulated first, which may be done by the software package referenced above, as well as several other packages, including Prolith by KLA-Tencor, HyperLith by Panoramic Technologies, among others.

The model for producing wafer images based on reticle near field images may include just the effect of the photolithography scanner, and it may also include the effect of resist, etch, CMP or any other wafer processes. One example process simulation model tool is Prolith available from KLA-Tencor Corp. of Milpitas, Calif. Resist and etch processes can be modeled rigorously or approximately. In a specific embodiment, the model may be in the form of a compact resist model that includes 3D acid diffusion inside a particular resist material and configuration, with boundary conditions imposed therewith, as well as a single threshold being applied to form the latent image.

It is noted that the modeled lithography tool may have a different illumination shape or source as the reticle inspection tool for acquiring actual images of the reticle. In certain embodiments, the modelled lithography tool may have a same or similar source as a reticle inspector tool.

Other simulation approaches such as SOCS or Abbe may be used. The algorithm generally known as the Sum Of Coherent Systems (SOCS) attempts to convert the imaging system into a bank of linear systems whose outputs are squared, scaled and summed. The SOCS method has been described elsewhere, including in the Ph.D. thesis of Nicolas Cobb, "Fast Optical and Process Proximity Correction Algorithms for Integrated Circuit Manufacturing", University of California, Berkeley, Spring, 1998. The Abbe algorithm includes calculating the image of the object for each point source, one at a time, and then summing up the intensity images together and taking the relative intensity of each source point into consideration.

The input for the model and its modeling parameters includes a set of process conditions that are applied to a recovered near field mask. That is, the model is configured to simulate different sets of process conditions on the reconstructed near field mask (or simulated mask image). Each set of process conditions generally corresponds to a set of wafer manufacturing process parameters that characterize, or partially characterize the wafer process for forming a wafer pattern from the mask. For example, a particular setting of focus and exposure can be input to the model. Other adjustable model parameters may also include one or more of the following parameters: a projection lens wavefront parameter, an apodization parameter, a chromatic aberrations focus error parameter, a vibration parameter, a resist profile index, a resist scum metric, top loss metric, etc. Use of such model with different sets of process conditions can result in a set of simulated wafer or resist pattern images formed by the reconstructed near field mask under different processing conditions, and these simulated wafer images can be used for pattern stability and defect detection assessment as further described herein.

A calibration reticle may also be used to fabricate a calibration wafer from which actual images are obtained in operation 216. In one example, the actual images are acquired using a critical dimension (CD) scanning electron microscope (SEM). Other imaging tools may be utilized, but a high resolution tool is preferred.

In general, the calibration wafer will contain any number of known structures, which may widely vary. The structures may be in the form of gratings which are typically periodic. Each grating may be periodic in one direction (X or Y) as, for example, a line space grating, or it may be periodic in two directions (X and Y) as, for example, a grid space grating. Examples of a grid space grating may include an array of lines in the Y direction with each line being segmented in the X direction. Another grid space example is an array of dot structures. That is, each structure may take the form of a line space grating, grid space grating, checkerboard pattern structure, etc. The structure design characteristics may each include line width (width at a specific height), line space width, line length, shape, side wall angle, height, pitch, grating orientation, top-profile (degree of top rounding or T topping), bottom profile (footing), etc. The calibration wafer may contain structures with different combinations of these feature characteristics. As should be appreciated, different structure characteristics (such as different widths, spacing, shapes, pitch, etc.) exhibit different response to focus and, therefore, the calibration mask preferably includes different structures with different characteristics.

In a specific embodiment, the calibration wafer may take the form of a "Design of Experiments (DOE)" wafer having different measurement sites that were subject to different processing conditions. In more general embodiments, process parameter variations are organized in a pattern on the surface of a semiconductor wafer (referred to as a DOE wafer). In this manner, the measurement sites correspond to different locations on the wafer surface having different associated process parameter values. In one example, the DOE pattern is a Focus/Exposure Matrix (FEM) pattern. Typically, a DOE wafer exhibiting a FEM pattern includes a grid pattern of measurement sites. In one grid direction (e.g., the x-direction), the exposure dosage is varied while the depth of focus is held constant. In the orthogonal grid direction (e.g., the y-direction), the depth of focus is varied while the exposure dosage is held constant. In this manner, measurement data collected from the FEM wafer includes data associated with known variations in the focus and dosage process parameters.

FEM measurement sites are generally located across the focus exposure matrix wafer. In fact, there may generally be one or more measurement sites per field. Each field may be formed using a different combination of focus and exposure (or may be focus or exposure only). For example, a first field may be produced using a first combination, and a second field may be produced using a second combination that is different than the first combination. The multiple combinations can be produced using varying focus and varying exposure, varying focus—constant exposure, constant focus—varying exposure, and the like.

The number of measurement sites may also differ. The number of sites per field is generally smaller on production wafers since the real estate on production wafers is so valuable. Also, fewer measurements are made on a product wafer than on a focus exposure matrix wafer due to time constraints in production. In one embodiment, a single site is measured per field. In another embodiment, multiple sites are measured per field.

In most FEM cases, the measurement site structures are formed from identically designed patterns using different processing parameters. It should be noted, however, that different focus exposure matrices may have different structures. For example, a first matrix may be performed using a first grating type and a second matrix may be performed using a second grating type that is different than the first grating type.

In an alternative embodiment, simulated calibration images (202) that are rendered from the design database for a calibration reticle may be used as input to the model. That is, the model can be calibrated without recovering the near-field from a physical calibration reticle. Instead, the lithography image is simulated by simulating (not recovering) the near field from the design database and applying the lithography imaging model to the simulated near field to arrive at the lithography result that is compared to the actual results from the wafer (216).

In general, optical signal data associated with known variations in any set of process parameters, structural parameters, or both, are contemplated. Regardless of form, the calibration wafer structures may be printed in a variety of different wafer layers. In particular, the printed structures are generally printed in a layer of photoresist using standard lithography processes (e.g., projecting a circuit image through a reticle and onto a silicon wafer coated with photoresist). The wafer may be a calibration wafer with layers of materials that correspond to the materials typically present on product wafers at that step in the test process. The printed structures may be printed over other structures in underlying layers. The calibration wafer may be a product wafer that has the potential to produce working devices. The calibration wafer may be a simple wafer that is only used for calibrating the model. The calibration wafer may be the same wafer that is used to calibrate the OPC design model. More than one calibration wafer may be used to calibrate the lithography model. When using multiple calibration wafers, the same or different calibration reticles may be used. The different calibration reticles may have patterns with different dimensions so as to produce a wider range of image data.

The process parameters used to form the calibration structures are generally configured to keep the pattern's characteristics within desired specifications. For example, the calibration structures may be printed on a calibration wafer as a part of a calibration procedure or they may be printed on a production wafer during production. In production, the calibration structures are typically printed in the scribe line between device areas (e.g., dies that define the IC) disposed on a production wafer. The measurement sites may be dedicated calibration structures disposed around the device structures or they may be a portion of the device structure (e.g., a periodic portion). As should be appreciated, using a portion of the device structure may be more difficult, but it tends to be more accurate since it is a portion of the device structure. In another embodiment, the calibration structures may be printed across an entire calibration wafer.

Referring back to FIG. 2, corresponding modeled and calibration results (e.g., images) may be compared in operation 210. It may then be determined whether the model parameters are to be adjusted in operation 212. If model parameters are to be adjusted, they are adjusted in operation 214 and the procedure 200 repeats the operation 208 for modeling the lithography process (and resist) using the adjusted parameters. Model parameters may be adjusted until a quantification of the differences between the model and calibration images have reached a minimum that is also below a predefined threshold. The quantity that is minimized can be the sum of squared differences between the acquired calibration images and the simulated images. The output of this process 200 is a lithography/resist model and its final model parameters. This set of model parameters, by the nature of using mask near field, overcomes the technical hurdle associated with mask process modeling and mask 3D diffraction calculation.

The simulated wafer patterns based on the recovered mask near field results may be used for a number of mask inspection, metrology, and/or qualification purposes. In one embodiment, a reticle qualification is performed by assessing whether the recovered mask near field will likely result in wafer pattern defects under a range of simulated wafer fabrication conditions. For defect detection, the printability of a reticle defect on the wafer is important, and the printability of reticle defects depends directly on the reticle near field and lithography system.

After a final calibrated lithography/resist/etch model for a particular process is obtained-regardless of how such model is obtained, such model may be used to generate accurate wafer plane resist images (e.g., after development or after etch) from a mask prior to wafer fabrication with such mask or for requalification of such mask. These resist images will allow one to assess the wafer images for any inspection patterns with high fidelity and through different focus and exposure settings or other lithography parameters. Since this assessment process can occur prior to wafer fabrication, qualification and defect detection cycles can be significantly shortened. Simulated wafer images may also enable separation of different patterning problem root causes by comparing the simulated wafer images after lithography, after resist model application, and after etch.

Figure 3:
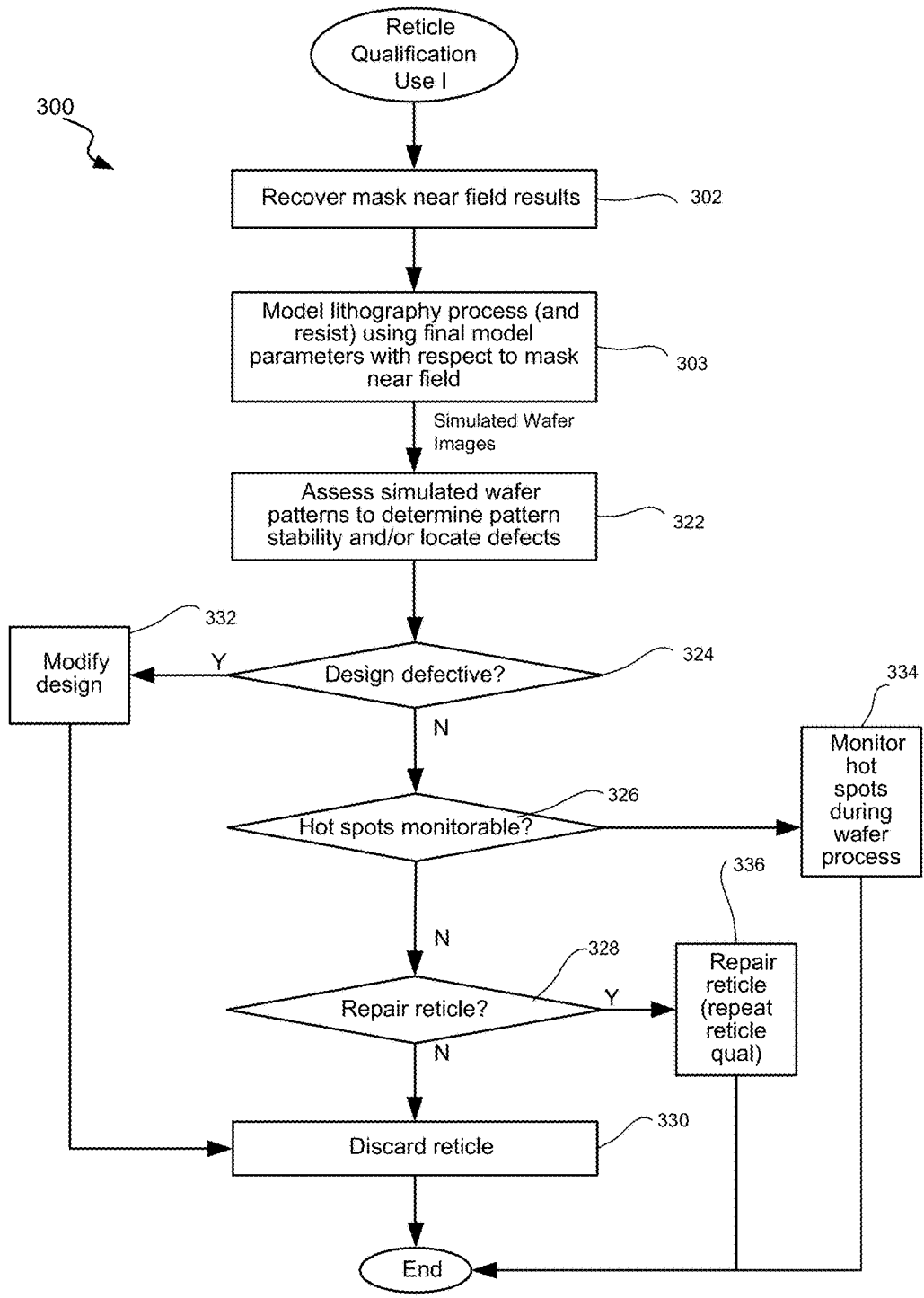
FIG. 3 illustrates a flow chart representing a reticle qualification process in accordance with one embodiment of the present invention.

FIG. 3 illustrates a flow chart representing a reticle qualification process 300 in accordance with one embodiment of the present invention. In operation 302, a mask near field image is recovered, e.g., for a particular reticle based on images acquired from such particular reticle. This operation may include the mask near field recovery operations of FIG. 1. After a mask near field is obtained, the lithography process (and resist) may also be modeled using the final model parameters with respect to the recovered near mask field in operation 303. For instance, the final model is used to simulate wafer images using a mask near field image.

The simulated wafer pattern may then be assessed to determine pattern stability and/or locate defects in operation 322. It may generally be determined whether the corresponding reticle will likely result in unstable or defective wafer patterns. In one embodiment, the model is applied to the mask near field image or results using a plurality of different process conditions, such as focus and dose, to assess the reticle design stability under varying process conditions.

Figure 4A:
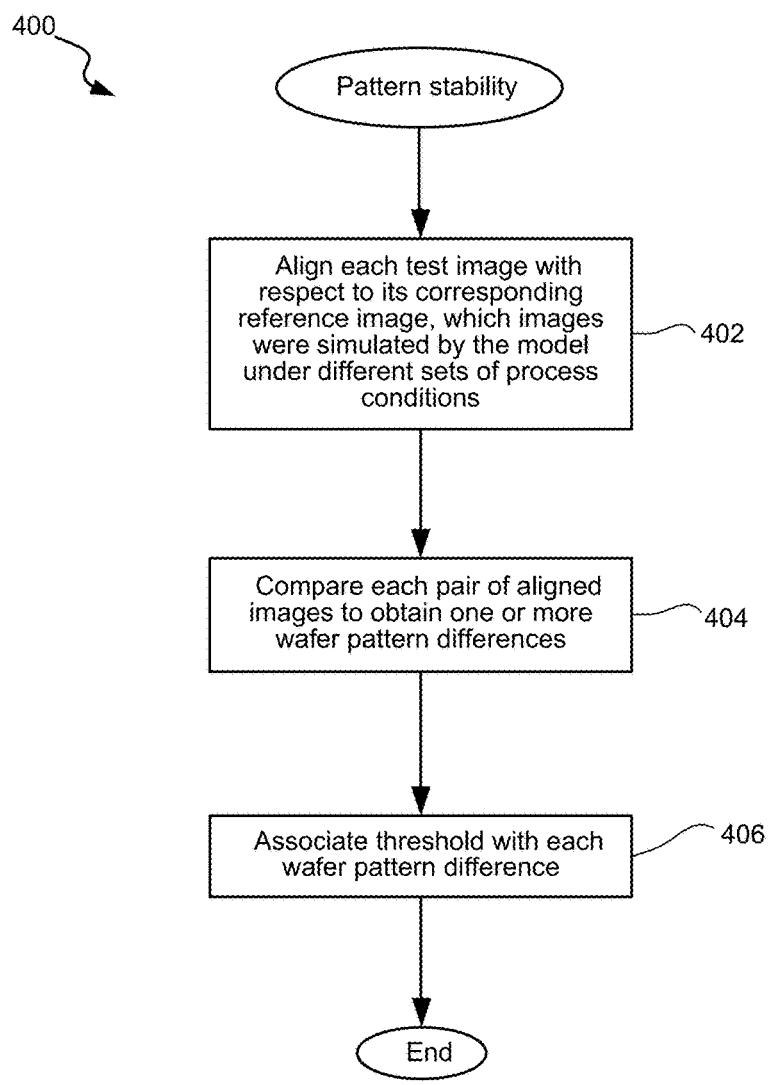
FIG. 4A is a flow chart illustrating a process for determining reticle pattern stability in accordance with an example application of the present invention.

FIG. 4A is a flow chart illustrating a process 400 for determining wafer pattern stability in accordance with an example application of the present invention. Initially, each test image may be aligned with its corresponding reference image, which images were also produced by the model under different sets of process conditions, in operation 402. The different test and reference images are calculated by the model under different processing conditions/parameters.

Each pair of aligned images may be compared to each other to obtain one or more wafer pattern differences in operation 404. Thresholds may then be associated with each wafer pattern difference in operation 406. The wafer pattern differences and their associated thresholds can be used together to characterize the pattern stability. That is, a particular pattern's amount of deviation (pattern differences) under different simulated process conditions and whether such deviation crosses an associated threshold together characterize pattern stability. The process window of a fabrication process specifies an expected or defined amount of process deviation under which the resulting patterns are assessed to ensure that they will remain stable or within certain specified tolerances of deviation (e.g., threshold).

Different thresholds for assessing pattern stability may be assigned to different areas of the reticle and, thereby, corresponding wafer patterns. The thresholds may all be the same or be different based on various factors, such as pattern design context, pattern MEEF (or Mask Error Enhancement Factor as described further below) level or sensitivity of the device performance to wafer pattern variation, etc. For instance, one may choose a tighter threshold for patterns in a dense region, compared to a semi-dense region of the reticle.

An initial set of hot spots or areas of pattern weakness may be optionally identified in both the reference and test mask pattern. For instance, a designer may provide a list of design hot spot coordinates that are critical to device function. For example, areas defined as hot spots may be assigned one detection threshold, while non-hot spot areas may be assigned a higher threshold (for defect detection). This differentiation can be used to optimize inspection resources.

This pattern stability assessment may be used to facilitate reticle qualification, thereby, overcoming many challenges in this field. As densities and complexities of integrated circuits (ICs) continue to increase, inspecting photolithographic mask patterns become progressively more challenging. Every new generation of ICs has denser and more complex patterns that currently reach and exceed optical limitations of lithographic systems. To overcome these optical limitations, various Resolution Enhancement Techniques (RET), such as Optical Proximity Correction (OPC), have been introduced. For example, OPC helps to overcome some diffraction limitations by modifying photomask patterns such that the resulting printed patterns correspond to the original desired patterns. Such modifications can include perturbations to sizes and edges of main IC features, i.e., printable features. Other modifications involve additions of serifs to pattern corners and/or providing nearby sub-resolution assist features (SRAFs), which are not expected to result in printed features and, therefore, are referred to as non-printable features. These non-printable features are expected to cancel pattern perturbations that would otherwise have occurred during the printing process. However, OPC makes mask patterns even more complex and usually very dissimilar to resulting wafer images. Furthermore, OPC defects often do not translate into printable defects. The increased complexity of the photomask pattern and fact that not all pattern elements are expected to directly affect the printed pattern makes the task of inspecting the photomask for meaningful pattern defects much more difficult. As the semiconductor industry moves to ever smaller features, leading-edge manufacturers are starting to use even more exotic OPC, such as inverse lithography technology (ILT), which result in highly complex patterns on the mask. Thus, it is highly desirable to know the mask writing fidelity and its wafer printing quality prior to physically making the wafer.

One measure of a defect's importance is its MEEF or Mask Error Enhancement Factor. This factor relates the size of the defect in the mask plane to the magnitude of the impact it will have on the printed image. High MEEF defects have high impact on the printed pattern; low MEEF defects have little or no impact on the printed pattern. An undersized main pattern feature in a dense fine-line portion of a pattern is an example of a defect with high MEEF where a small mask plane sizing error could cause a complete collapse of the printed pattern. An isolated small pinhole is an example of a defect with low MEEF where the defect itself is too small to print and is distant enough from the nearest main pattern edge so as not to affect how that edge is printed. As these examples show the MEEF of a defect is a somewhat complicated function of the defect type and the pattern context in which the defect is located.

In addition to higher MEEF mask defects causing more significant wafer defects, certain design patterns and corresponding mask patterns may be more robust than other design and mask patterns to process changes. When the fabrication process begins to drift from optimal process conditions, certain mask patterns may result in more significant wafer pattern perturbations and defects.

Figure 4B:
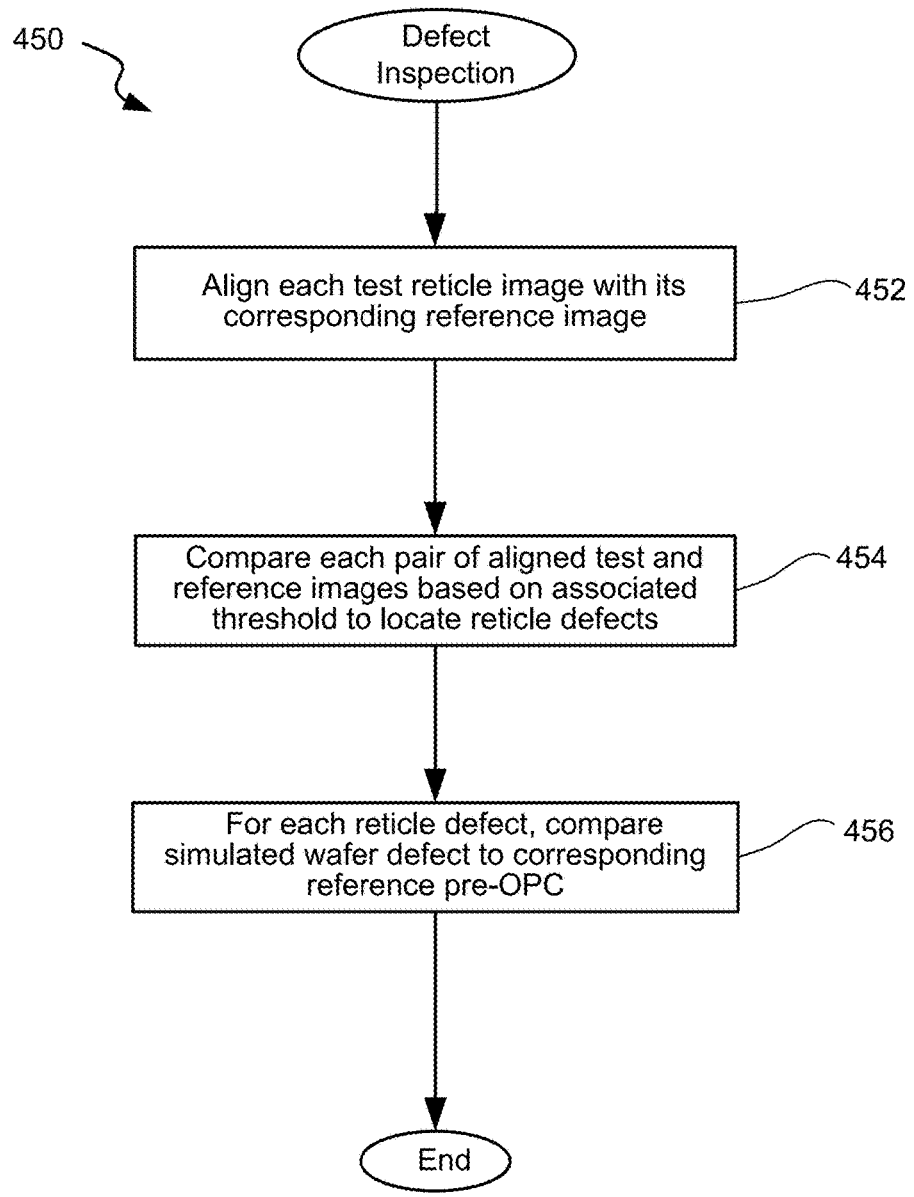
FIG. 4B is a flow chart illustrating a defect inspection procedure in accordance with an another embodiment of the present invention.

FIG. 4B is a flow chart illustrating a defect inspection procedure 450 in accordance with another embodiment of the present invention. In operation 452, each modelled test wafer image may be aligned with its corresponding reference image. In one embodiment, a die-to-die or cell-to-cell alignment may be accomplished. In another embodiment, the modelled test wafer image is aligned with a rendered reference image from the corresponding post-OPC design. For instance, the post-OPC design is processed so as to simulate the reticle fabrication process for such design. For example, corners are rounded. In general, a reference image may originate from the same die as the test image at an earlier time, from an adjacent identical die, or rendered from the design database. In a specific example, the reference image is obtained from a "golden" die, which was proven to be without defects (e.g., immediately after the reticle was manufactured and qualified). The golden reticle images, which were obtained from the reticle when it was known to not be defective, can be stored and later used to compute the golden reticle near field images and wafer images on demand when needed. Alternatively, the golden reticle near field images can be stored for ready access without the need to re-compute the near field in future inspections.

Each pair of aligned test and reference images is compared based on an associated threshold to locate reticle defects in operation 454. Any suitable mechanism may be used to associate thresholds to particular reticle areas as further described above. Any suitable metrics of the test and reference images may be compared. For instance, the contour of test and reference wafer images can be compared as a metric for edge placement error (EPE).

For each reticle defect, the corresponding simulated wafer defect area may then be compared to its corresponding reference pre-OPC area in operation 456. That is, the simulated wafer patterns are assessed to determine whether the reticle defect results in a wafer defect that varies from the intended design.

Referring back to FIG. 3, it may then be determined whether the design is defective based on the simulated reticle images in operation 324. In one embodiment, it is determined whether the design pattern results in unacceptable wafer pattern variation under a specified range of process conditions (or process window). It is determined whether there is a significant difference due to process variability. If the difference between differently processed wafer patterns is higher than a corresponding threshold, such wafer patterns may be deemed defective. These systematic defects are known as hot spots. It may also be determined whether any difference between a simulated wafer pattern from reticle and its corresponding pre-OPC pattern is above a predefined threshold. If the design is determined to be defective, the design may be modified in operation 332.

Once a reticle's design has been verified, the reticle may likely still contain hot spot that should be monitored. The following operations are described as being implemented on a mask for which there are at least some identified hot spots. Of course, if the mask does not contain any identified hot spots, the following operations of FIG. 3 may be skipped and the mask used without hot spot monitoring being performed during fabrication and inspection.

In the illustrated example, if the design is not deemed defective, it may then be determined whether any hot spots can be monitored in operation 326. If it is determined that the hot spots can be monitored, the hot spots may then be monitored during the wafer process in operation 334. For instance, the hot spot patterns may be monitored during wafer fabrication to determine whether the process has drifted out of specification and has caused the corresponding wafer pattern to have critical parameters that change to unacceptable values. One implementation may involve setting a relatively high MEEF level for inspection of the corresponding hot spot's reticle and/or wafer pattern. As conditions get further away from nominal process conditions, CD or EPE can become large and endanger the integrity of the wafer manufacturing process.

Hot spot patterns may be identified merely when a test mask pattern changes by a predefined amount regardless of how such change compares to the original intended design (e.g., pre-OPC data). In other words, a significant change in the physical mask pattern under different process conditions may indicate a problem with the intended design pattern. Differences between the corresponding modeled image portions represent differences in the effect of the process conditions on the designed pattern and the manufactured mask. Differences associated with a particular design pattern are commonly referred to as "design hot spots", or just "hot spots", and represent weak points in the design with respect to the particular process conditions that have been examined, maybe also, with respect to the manufactured mask. Examples of the kinds of differences that might be found between modeled images for different process conditions are CD (critical dimension) or EPE (edge placement error).

In another embodiment, if the model is applied to the post-OPC design database, the resulting wafer pattern can correspond to the pattern that is intended by the designer to be printed on the wafer. Optionally, the results from applying the model to the post-OPC database can be used with the modeled images to improve hot spot detection. For example, a model of the post-OPC database takes into account design effects only, and so can be used to separate the effect of the wafer process on the design and the effect of the wafer process on the manufactured mask. Modelled patterns from the mask near field may be compared to modelled wafer images from corresponding post-OPC patterns. For instance, when a set of modelled wafer patterns for different process changes match corresponding modelled post-OPC wafer patterns for the same process changes, the changes in wafer pattern (or resist pattern) due to process change can be determined to originate from the design pattern, which can be redesigned or monitored, rather than from a defect in the mask pattern. However, if the changes on wafer due to process variations from the post-OPC database are different from those on wafer due to the same process variations from the recovered mask (or mask near field), then these hot spots are considered originating from a hot spot from the actual mask, which can be repaired or monitored.

The simulated wafer image differences may also be analyzed to determine wafer CD uniformity (CDU) metrics across the die or over time as reticle changes occur during exposure in the fabrication process. For example, the CD can be measured for each target of each image by analyzing and measuring the distance between the target edges if the resolution is high enough. Alternatively, the intensity differences between reference and test images may be calibrated and transformed into CD variations as described further in U.S. patent application Ser. No. 14/664,565 filed 20 Mar. 2015 by Carl E. Hess et al. and U.S. patent application Ser. No. 14/390,834 filed 6 Oct. 2014 by Ruifang Shi et al., which applications are incorporated herein by reference in their entirety for all purposes.

It may also be determined whether the reticle is to be repaired in operation 328. The anticipated wafer pattern variations may be determined to be out of specification for the process window that is expected to be used during the lithography process. In certain cases, the reticle may contain a defect that is repaired in operation 336. The reticle may then be requalified. Otherwise, the reticle may be discarded if it is not repairable in operation 330. A new reticle may then be manufactured and requalified.

Figure 5:
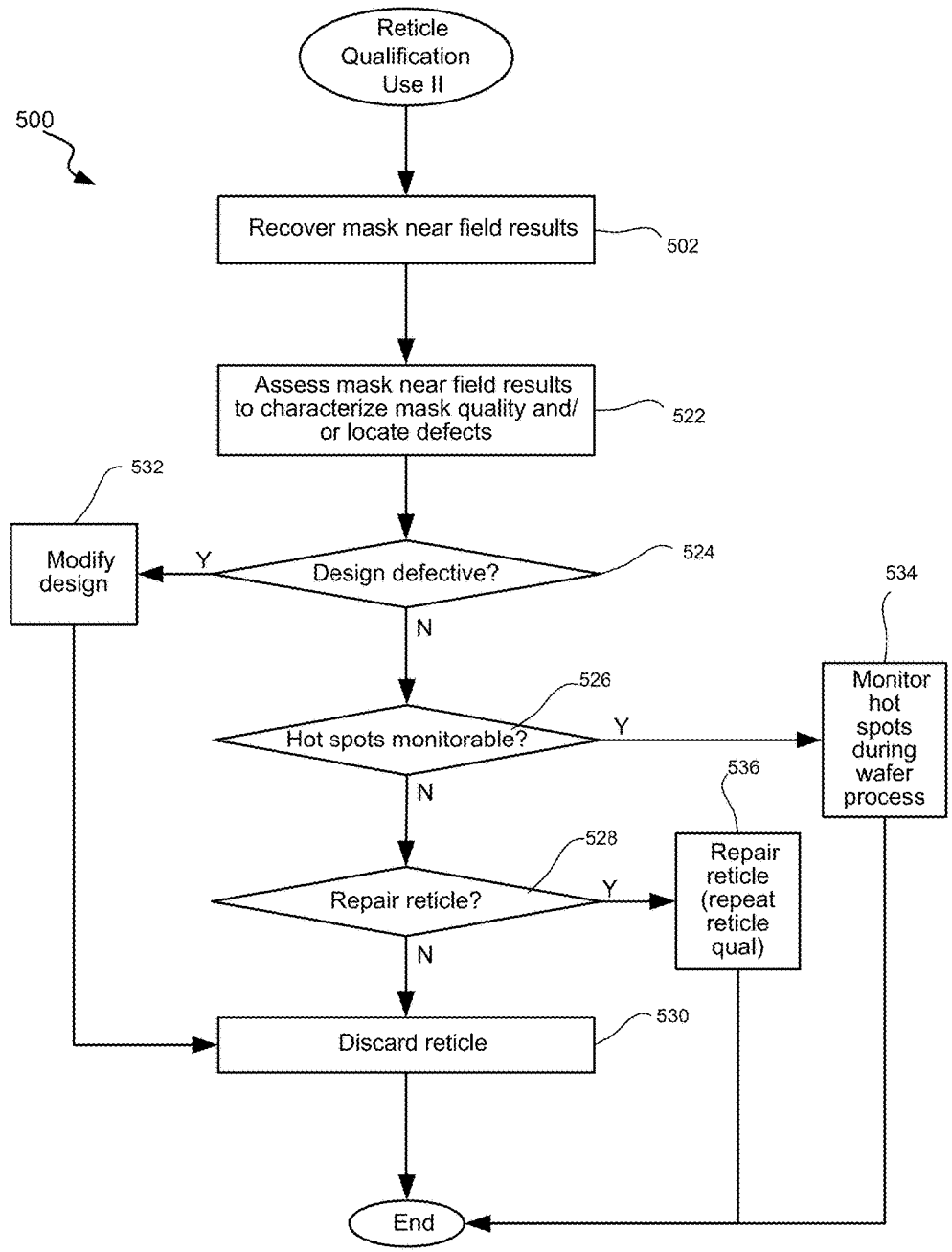
FIG. 5 is a flow chart illustrated a reticle qualification process that is applied to a recovered mask near field image or results in accordance with an alternative embodiment of the present invention.

In addition or alternatively to using a recovered mask near field image for simulating wafer images in a qualification process, a mask near field image or results may also be assessed directly in a reticle qualification process. FIG. 5 is a flow chart illustrated a reticle qualification process 500 that is applied to a recovered mask near field image or results in accordance with an alternative embodiment of the present invention. Initially, mask near field results are recovered from a reticle in operation 502. This mask near field image may be recovered for a particular reticle based on images acquired from such particular reticle. This operation may be practiced similar to the mask near field recover operations of FIG. 1. Additionally, several of the operations of FIG. 5 may be implemented in a similar manner as operations of FIG. 3, but with to the recovered reticle near field image, including intensity and/or phase components of such image.

As shown, the mask near field results may then be assessed to characterize and/or locate defects in operation 522. It may generally be determined whether the corresponding reticle is defective or has hot spots that need monitoring. More specifically, some of the techniques described herein for assessing the simulated wafer images may be implemented on the mask near field images. In a defect detection process, any suitable metrics of test and reference mask near field images may be compared. For instance, intensity and/or phase may be compared. Different defect types will have different impacts on intensity and/or phase values. These differences can be determined to be real defects (as opposed to non-impacting nuisance defects) that will likely result in a defective wafer or identify hot spot patterns or areas that are repairable or monitorable.

For instance, it may then be determined whether the design is defective in operation 524. If the design is determined to be defective, the design may be modified in operation 532. For instance, it may be determined whether any difference between a reticle near field image and its corresponding post-OPC-based near field is above a predefined threshold for detecting defects. The procedure 500 may continue so as to determine whether to monitor wafer hot spots, repair the reticle, or redesign the reticle as described above. If the design is not deemed defective, it may then be determined whether any hot spots can be monitored in operation 526. For example, it may be determined that any intensity and/or phase difference between a test and reference reticle near field image is close to an associated threshold.

If it is determined that the hot spots can be monitored, the hot spots may then be monitored during the wafer process in operation 534, for instance. For instance, the hot spot patterns may be monitored during wafer fabrication to determine whether the process has drifted out of specification and has caused the corresponding wafer pattern to have critical parameters that change to unacceptable values. One implementation may involve setting a relatively high sensitivity level for inspection of the corresponding hot spot's reticle and/or wafer pattern. As conditions get further away from nominal process conditions, CD error or EPE can become large and endanger the integrity of the wafer manufacturing process.

It may also be determined whether the reticle is to be repaired in operation 528. In certain cases, the reticle may contain a defect that is repaired in operation 536. The reticle may then be requalified. Otherwise, the reticle may be discarded if it is not repairable in operation 530. A new reticle may then be manufactured and requalified.

Certain techniques of the present invention provide mask pattern qualification and early detection of weak patterns or hot spots on the physical mask before beginning wafer manufacturing. In addition to providing recovery of the reticle near field based on reticle images, a full range of wafer process effects (including many settings of focus and exposure, and the effect of wafer resist, etch, CMP, and any other wafer processes) can be considered for how they affect the wafer patterns. No prior knowledge of the mask is required since the mask near field is recovered using only reticle images without using reticle design data. Since mask patterns are generally 4× larger than wafer patterns, more exact locations of patterns with respect to the design database can be determined. The above techniques can also be extended to any suitable type of masks, such as pattern qualification of EUV masks.

Figure 6:
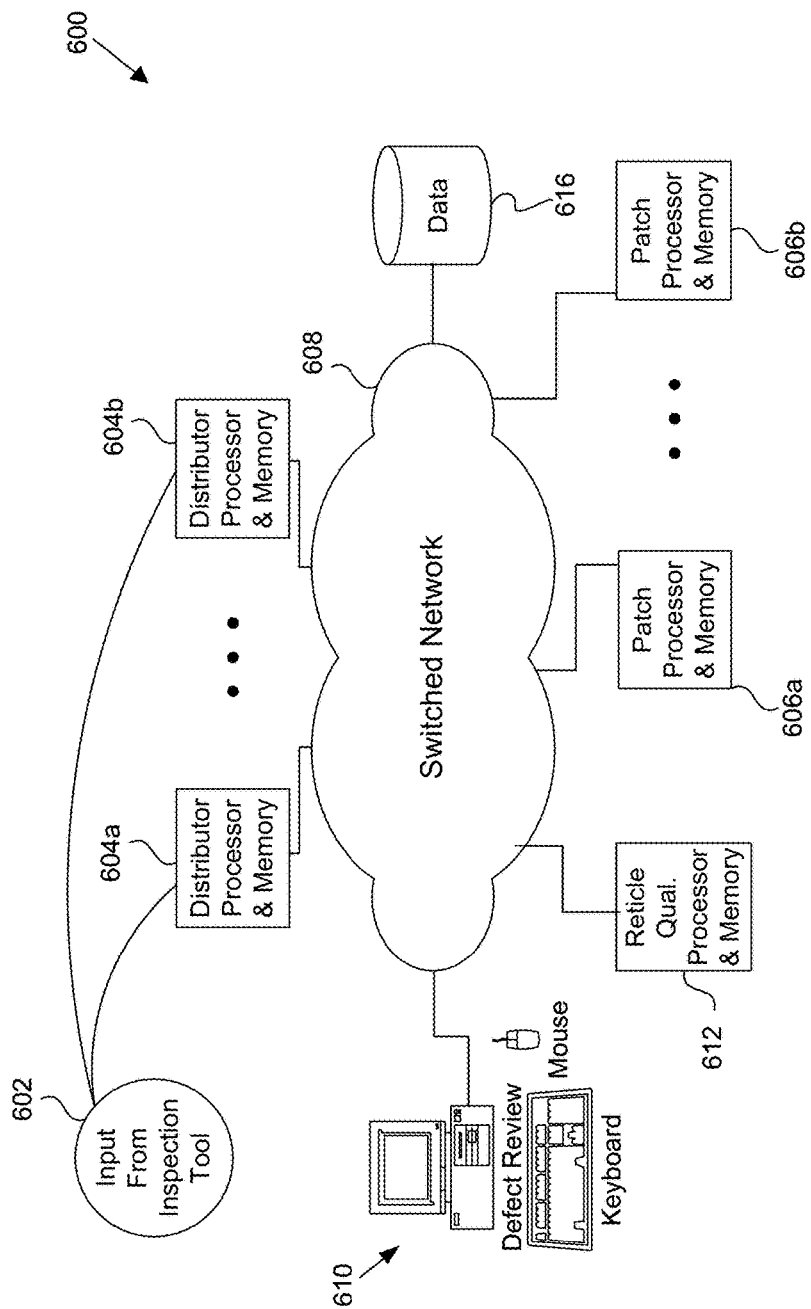
FIG. 6 is a diagrammatic representation of an example inspection system in which techniques of the present invention may be implemented.

Techniques of the present invention may be implemented in any suitable combination of hardware and/or software. FIG. 6 is a diagrammatic representation of an example inspection system 600 in which techniques of the present invention may be implemented. The inspection system 600 may receive input 602 from a high NA inspection tool or a low NA inspector mimicking a scanner (not shown). The inspection system may also include a data distribution system (e.g., 604a and 604b) for distributing the received input 602, an intensity signal (or patch) processing system (e.g., patch processors and reticle qualification system 612) for mask near field and wafer recovery, process modelling, etc., a network (e.g., switched network 608) for allowing communication between the inspection system components, an optional mass storage device 616, and one or more inspection control and/or review stations (e.g., 610) for reviewing mask near field intensity and phase (values, images, or differences), reticle/wafer images, identified hot spots, CD, CDU maps, process parameters, etc. Each processor of the inspection system 600 typically may include one or more microprocessor integrated circuits and may also contain interface and/or memory integrated circuits and may additionally be coupled to one or more shared and/or global memory devices.

The inspector or data acquisition system (not shown) for generating input data 602 may take the form of any suitable instrument (e.g., as described further herein) for obtaining intensity signals or images of a reticle. For example, the low NA inspector may construct an optical image or generate intensity values of a portion of the reticle based on a portion of detected light that is reflected, transmitted, or otherwise directed to one or more light sensors. The low NA inspector may then output the intensity values or image.

The low NA inspection tool may be operable to detect and collect reflected and/or transmitted light as an incident optical beam scans across each patch of a reticle. As noted above, the incident optical beam may scan across reticle swaths that each comprises a plurality of patches. Light is collected in response to this incident beam from a plurality of points or subareas of each patch.

The low NA inspection tool may be generally operable to convert such detected light into detected signals corresponding to intensity values. The detected signals may take the form of an electromagnetic waveform having amplitude values that correspond to different intensity values at different locations of the reticle. The detected signals may also take the form of a simple list of intensity values and associated reticle point coordinates. The detected signals may also take the form of an image having different intensity values corresponding to different positions or scan points on the reticle. Two or more images of the reticle may be generated after all the positions of the reticle are scanned and converted into detected signals, or portions of two or more images may be generated as each reticle portion is scanned with the final two or more images for the reticle being complete after the entire reticle is scanned.

The detected signals may also take the form of aerial images. That is, an aerial imaging technique may be used to simulate the optical effects of the photolithography system so as to produce an aerial image of the photoresist pattern that is exposed on the wafer. In general, the optics of the photolithography tool are emulated so as to produce an aerial image based on the detected signals from the reticle. The aerial image corresponds to the pattern produced from the light passed through the photolithography optics and reticle onto the photoresist layer of a wafer. Additionally, the photoresist exposure process for the particular type of photoresist material may also be emulated.

The incident light or detected light may be passed through any suitable spatial aperture to produce any incident or detected light profile at any suitable incident angles. By way of examples, programmable illumination or detection apertures may be utilized to produce a particular beam profile, such as dipole, quadrapole, quasar, annulus, etc. In a specific example, Source Mask Optimization (SMO) or any pixelated illumination technique may be implemented. The incident light may also be passed through a linear polarizer for linearly polarizing all or a portion of the illumination pupil in one or more polarizations. The detected light may be passed through apodization components for blocking particular areas of the collection beam.

Intensity or image data 602 can be received by data distribution system via network 608. The data distribution system may be associated with one or more memory devices, such as RAM buffers, for holding at least a portion of the received data 602. Preferably, the total memory is large enough to hold an entire swatch of data. For example, one gigabyte of memory works well for a swatch that is 1 million by 1000 pixels or points.

The data distribution system (e.g., 604a and 604b) may also control distribution of portions of the received input data 602 to the processors (e.g. 606a and 606b). For example, data distribution system may route data for a first patch to a first patch processor 606a, and may route data for a second patch to patch processor 606*b*. Multiple sets of data for multiple patches may also be routed to each patch processor.

The patch processors may receive intensity values or an image that corresponds to at least a portion or patch of the reticle. The patch processors may each also be coupled to or integrated with one or more memory devices (not shown), such as DRAM devices that provide local memory functions, such as holding the received data portion. Preferably, the memory is large enough to hold data that corresponds to a patch of the reticle. For example, eight megabytes of memory works well for intensity values or an image corresponding to a patch that is 512 by 1024 pixels. Alternatively, the patch processors may share memory.

Each set of input data 602 may correspond to a swath of the reticle. One or more sets of data may be stored in memory of the data distribution system. This memory may be controlled by one or more processors within the data distribution system, and the memory may be divided into a plurality of partitions. For example, the data distribution system may receive data corresponding to a portion of a swath into a first memory partition (not shown), and the data distribution system may receive another data corresponding to another swath into a second memory partition (not shown). Preferably, each of the memory partitions of the data distribution system only holds the portions of the data that are to be routed to a processor associated with such memory partition. For example, the first memory partition of the data distribution system may hold and route first data to patch processor 606*a*, and the second memory partition may hold and route second data to patch processor 606*b*.

The data distribution system may define and distribute each set of data of the data based on any suitable parameters of the data. For example, the data may be defined and distributed based on the corresponding position of the patch on the reticle. In one embodiment, each swath is associated with a range of column positions that correspond to horizontal positions of pixels within the swath. For example, columns 0 through 256 of the swath may correspond to a first patch, and the pixels within these columns will comprise the first image or set of intensity values, which is routed to one or more patch processors. Likewise, columns 257 through 512 of the swath may correspond to a second patch, and the pixels in these columns will comprise the second image or set of intensity values, which is routed to different patch processor(s).

The inspection apparatus may be suitable for inspecting semiconductor devices or wafers and optical reticles, as well as EUV reticles or masks. Examples of suitable inspection tools are the Teron™ operating at 193 nm or the TeraScan™ DUV reticle inspection tools available from KLA-Tencor of Milpitas, Calif. Other types of samples which may be inspected or imaged using the inspection apparatus of the present invention include any surface, such as a flat panel display.

An inspection tool may include at least one light source for generating an incident light beam, illumination optics for directing the incident beam onto a sample, collection optics for directing an output beam that is emitted from the sample in response to the incident beam, a sensor for detecting the output beam and generating an image or signal for the output beam, and a controller/processor for controlling the components of the inspection tool and facilitating the mask near field generation and analysis techniques as described further herein.

In the following exemplary inspection systems, the incident beam may be in any suitable form of coherent light. Additionally, any suitable lens arrangement may be used to direct the incident beam towards the sample and direct the output beam emanating from the sample towards a detector. The output beam may be reflected or scattered from the sample or transmitted through the sample. For EUV reticle inspection, the output beam is typically reflected from the sample. Likewise, any suitable detector type or number of detection elements may be used to receive the output beam and provide an image or a signal based on the characteristics (e.g., intensity) of the received output beam.

Figure 7A:
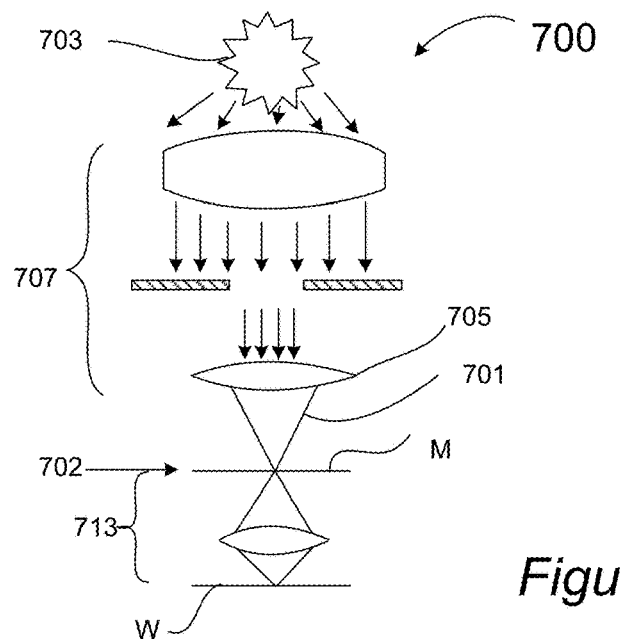
FIG. 7A is a simplified schematic representation of a lithographic system for transferring a mask pattern from a photomask onto a wafer in accordance with certain embodiments.

A generalized photolithography tool will first be described although an EUV photolithography tool would typically only have reflecting type optics. FIG. 7A is a simplified schematic representation of a typical lithographic system 700 that can be used to transfer a mask pattern from a photomask M onto a wafer W in accordance with certain embodiments. Examples of such systems include scanners and steppers, more specifically the TWINSCAN NXT: 1970Ci Step-and-Scan system available from ASML in Veldhoven, Netherlands. In general, an illumination source 703 directs a light beam through an illumination optics 707 (e.g., lens 705) onto a photomask M located in a mask plane 702. Illumination lens 705 has a numeric aperture 701 at that plane 702. The value of the numerical aperture 701 impacts which defects on the photomask are lithographic significant defects and which ones are not. A portion of the beam that passes through the photomask M forms a patterned optical signal that is directed through imaging optics 713 and onto a wafer W to initiate the pattern transfer. In a reflecting system (not shown), the illumination beam is reflected from certain portions of the mask M (and absorbed by other portions of such mask M) and forms a patterned signal that is directed through reflecting imaging optics on a wafer W.

Figure 7B:
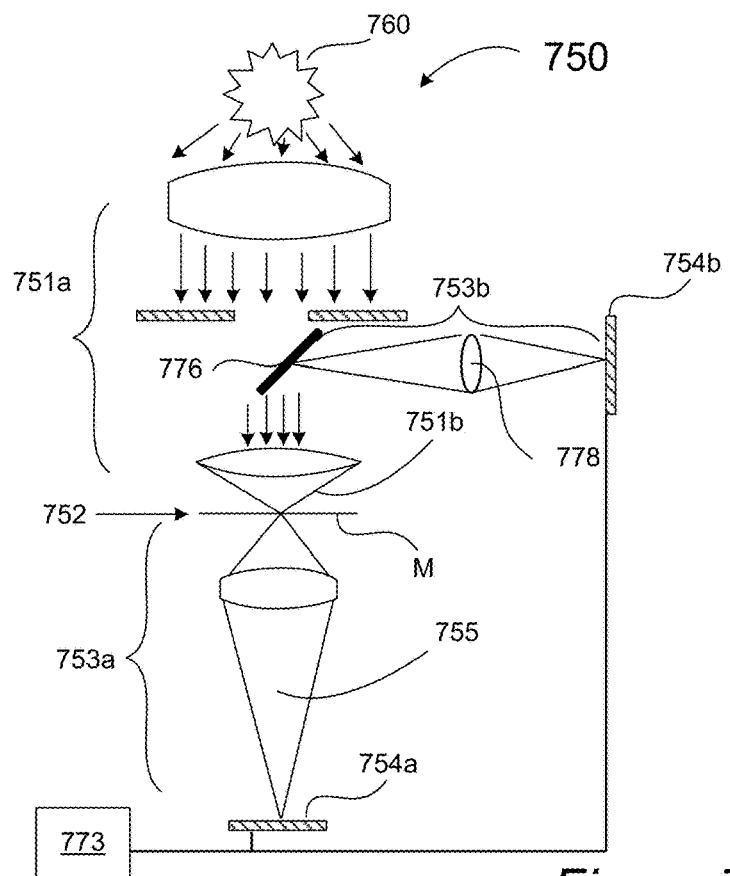
FIG. 7B provides a schematic representation of a photomask inspection apparatus in accordance with certain embodiments.

The inspection tool may utilize similar components or be similarly configured as the above-described photolithography tool, e.g., LNI capability. However, the inspection tool may be alternatively or additionally configurable to generate high resolution images. FIG. 7B provides a schematic representation of an example inspection system 750 that has illumination optics 751*a* includes an imaging lens with a relative large numerical aperture 751*b* at a reticle plane 752 in accordance with certain embodiments. For example, numerical aperture 751*b* at the reticle plane 752 of the inspection system may be considerable greater than the numerical aperture 701 at the reticle plane 702 of the lithography system 700, which would result in differences between test inspection images and actual printed images.

The inspection techniques described herein may be implemented on various specially configured inspection systems, such as the one schematically illustrated in FIG. 7B. The illustrated system 750 includes an illumination source 760 producing a light beam that is directed through illumination optics 751*a* onto a photomask M in the reticle plane 752. Examples of light sources include a coherent laser light source (e.g., deep UV or gas laser generator), a filtered lamp, LED light source, etc. In certain embodiments, a light source may generally provide high pulse repetition rate, low-noise, high power, stability, reliability, and extendibility. It is noted that while an EUV scanner operates at 13.5 nm wavelength, an inspection tool for an EUV reticle does not have to operate at the same wavelength although it could. In one example, the source is a 193 nm laser. It is noted that if the mask near field is recovered at the same wavelength as used in the photolithography tool, the resulting near field results can then be used for predicting a wafer image (e.g., for both ArF and EUV reticles) as well as defect detection. If the near field is recovered at a different wavelength than the photolithography tool or uses reflected light for 193 nm transmission photolithography, however, the near field results may not be used for predicting a wafer image but can still be used for defect detection.

The illumination optics 751a may include a beam steering device for precise beam positioning and a beam conditioning device, which can be used to provide light level control, speckle noise reduction, and high beam uniformity. Beam steering and/or beam conditioning devices may be separate physical devices from, for example, a laser. The illumination optics 751a may also include optics for controlling polarization, focus, magnification, illumination intensity distributions, etc.

As explained above, the inspection system 750 may have a numerical aperture 751b at the reticle plane 752 that may be equal to or greater than a reticle plane numerical aperture (e.g., element 701 in FIG. 7A) of the corresponding lithography system. The photomask M to be inspected is placed on a mask stage at the reticle plane 752 and exposed to the source.

The depicted inspection system 750 may include detection optics 753a and 753 b, which may also include microscopic magnification optics designed to provide, for example, 60-200× magnification or more for enhanced inspection. The collection optics 753a and 753b may include any suitable optics for conditioning the output light/beam. For instance, the collection optics 753a and 753b may include optics for controlling focus, pupil shapes, polarization analyzer settings, etc.

In a transmitting mode, the patterned image from the mask M may be directed through a collection of optical elements 753a, which project the patterned image onto a sensor 754a. In a reflecting mode, collection elements (e.g., beam splitter 776 and detection lens 778) direct and capture the reflected light from the mask M onto sensor 754b. Although two sensors are shown, a single sensor can be used to detect reflected and transmitted light during different scans of the same reticle area. Suitable sensors include charged coupled devices (CCD), CCD arrays, time delay integration (TDI) sensors, TDI sensor arrays, photomultiplier tubes (PMT), and other sensors.

The illumination optics column may be moved with respect to the mask stage and/or the stage moved relative to a detector or camera by any suitable mechanism so as to scan patches of the reticle. For example, a motor mechanism may be utilized to move the stage. The motor mechanism may be formed from a screw drive and stepper motor, linear drive with feedback position, or band actuator and stepper motor, by way of examples. The system 700 may utilize one or more motor mechanisms for moving any of the system components with respect to the illumination or collection optical paths.

The signals captured by each sensor (e.g., 754a and/or 754b) can be processed by a computer system 773 or, more generally, by one or more signal processing devices, which may each include an analog-to-digital converter configured to convert analog signals from each sensor into digital signals for processing. The computer system 773 typically has one or more processors coupled to input/output ports, and one or more memories via appropriate buses or other communication mechanisms.

The computer system 773 may also include one or more input devices (e.g., a keyboard, mouse, joystick) for providing user input, such as changing focus and other inspection recipe parameters. The computer system 773 may also be connected to the stage for controlling, for example, a sample position (e.g., focusing and scanning) and connected to other inspection system components for controlling other inspection parameters and configurations of such inspection system components.

The computer system 773 may be configured (e.g., with programming instructions) to provide a user interface (e.g., a computer screen) for displaying mask near field intensity and phase (values, images, or differences), reticle/wafer images, identified hot spots, CD, CDU maps, process parameters, etc. The computer system 773 may be configured to analyze intensity, phase, and/or other characteristics of reflected and/or transmitted detected and/or simulated signals or images, recovered reticle near field results, etc. The computer system 773 may be configured (e.g., with programming instructions) to provide a user interface (e.g., on a computer screen) for displaying resultant intensity and/or phase values, images, and other inspection characteristics. In certain embodiments, the computer system 773 is configured to carry out inspection techniques detailed above.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

FIG. 7B shows an example where an illuminating light beam is directed towards the sample surface at a substantially normal angle with respect to the inspected surface. In other embodiments, an illuminating light beam can be directed at an oblique angle, which allows separation of the illuminating and reflected beams. In these embodiments, an attenuator may be positioned on the reflected beam path in order to attenuate a zero order component of the reflected light beam prior to reaching a detector. Furthermore, an imaging aperture may be positioned on the reflected beam path to shift the phase of the zero order component of the reflected light beam.

It should be noted that the above description and drawings are not to be construed as a limitation on the specific components of the system and that the system may be embodied in many other forms. For example, it is contemplated that the inspection or measurement tool may have any suitable features from any number of known imaging or metrology tools arranged for detecting defects and/or resolving the critical aspects of features of a reticle or wafer. By way of example, an inspection or measurement tool may be adapted for bright field imaging microscopy, dark field imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may also be contemplated as forming part of the inspection or metrology apparatus.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of qualifying a photolithographic reticle, the method comprising:
    using an imaging tool to acquire a plurality of images at different illumination configurations and/or different imaging configurations from each of a plurality of pattern areas of a test reticle;
    recovering a reticle near field for each of the pattern areas of the test reticle based on the acquired images from each pattern area of the test reticle; and
    using the recovered reticle near field to determine whether the test reticle or another reticle will likely result in an unstable wafer pattern or a defective wafer.

2. The method of claim 1, wherein the reticle near field is directly analyzed to determine whether the test reticle or another reticle will likely result in an unstable wafer pattern or a defective wafer.

3. The method of claim 1, wherein the plurality of images are acquired at a field or pupil plane.

4. The method of claim 1, wherein the recovered reticle near field is used to detect defects in the test reticle or in simulated wafer images that are simulated from the recovered reticle near field, wherein defect detection including comparing intensity and/or phase for a same die at different times, for adjacent dies, for a die and its corresponding golden die, or for a die and a corresponding die from a reticle copy with an identical design to the test reticle.

5. The method of claim 1, wherein the reticle near field is recovered without using a design database that was used to fabricate the test reticle.

6. The method of claim 1, wherein the acquired images include at least three reflective images that are acquired at different imaging conditions that are selected to result in a same reticle near field, and wherein the different imaging conditions include different focus settings, different pupil shapes, or polarization analyzer settings, wherein the different illumination conditions include different source intensity distribution and/or polarization settings.

7. The method of claim 1, wherein the acquired images include at least three transmitted images that are acquired at different imaging conditions that are selected to result in a same reticle near field, and wherein the different imaging conditions include different focus settings, different pupil shapes, or polarization analyzer settings, wherein the different illumination conditions include different source intensity distribution and/or polarization settings.

8. The method of claim 1, further comprising:
    applying a lithography model to the reticle near field for the test reticle to simulate a plurality of test wafer images, and
    analyzing the simulated test wafer images to determine whether the test reticle will likely result in an unstable or defective wafer,
    wherein the lithography model is configured to simulate a photolithography process.

9. The method of claim 8, wherein the lithography model simulates an illumination source having a different shape than an illumination shape of an inspection tool for acquiring images of the test reticle or another reticle or wafer.

10. The method of claim 8, wherein the lithography model is calibrated with images rendered from a design database for a calibration reticle.

11. The method of claim 8, wherein the lithography model is calibrated with images acquired from a calibration reticle.

12. The method of claim 8, wherein the lithography model includes a compact resist model.

13. The method of claim 8, wherein the lithography model is applied to the reticle near field, which was recovered for the test reticle, under a plurality of different lithography process conditions, and wherein analyzing the simulated test wafer images includes determining whether the test reticle will likely result in an unstable wafer under the different lithography process conditions by comparing portions of the simulated test images associated with different process conditions and a same reticle area.

14. An imaging system for qualifying a photolithographic reticle, the system comprising:
    a light source for generating an incident beam;
    an illumination optics module for directing the incident beam onto a reticle;
    a collection optics module for directing an output beam from each pattern area of the reticle to at least one sensor;
    at least one sensor for detecting the output beam and generating an image or signal based on the output beam; and
    a controller that is configured to perform the following operations:
        causing the acquiring of plurality of images at different illumination configurations and/or different imaging configurations from each of a plurality of pattern areas of a test reticle;
        recovering a reticle near field for each of the pattern areas of the test reticle based on the acquired images from each pattern area of the test reticle; and
        using the recovered reticle near field to determine whether the test reticle or another reticle will likely result in an unstable wafer pattern or a defective wafer.

15. The system of claim 14, wherein the reticle near field is directly analyzed to determine whether the test reticle or another reticle will likely result in an unstable wafer pattern or a defective wafer.

16. The system of claim 14, wherein the plurality of images are acquired at a field or pupil plane.

17. The system of claim 14, wherein the recovered reticle near field is used to detect defects in the test reticle or in simulated wafer images that are simulated from the recovered reticle near field, wherein defect detection including comparing intensity and/or phase for a same die at different times, for adjacent dies, for a die and its corresponding golden die, or for a die and a corresponding die from a reticle copy with an identical design to the test reticle.

18. The system of claim 14, wherein the reticle near field is recovered without using a design database that was used to fabricate the test reticle.

19. The system of claim 14, wherein the acquired images include at least three reflective images that are acquired at different imaging conditions that are selected to result in a same reticle near field, and wherein the different imaging conditions include different focus settings and different pupil shapes.

20. The system of claim 14, wherein the acquired images include at least three transmitted images that are acquired at different imaging conditions that are selected to result in a same reticle near field, and wherein the different imaging conditions include different focus settings and different pupil shapes.

21. The system of claim 14, wherein the controller is further configured for:
 applying a lithography model to the reticle near field for the test reticle to simulate a plurality of test wafer images, and
 analyzing the simulated test wafer images to determine whether the test reticle will likely result in an unstable or defective wafer,
 wherein the lithography model is configured to simulate a photolithography process.

22. The system of claim 21, wherein the lithography model simulates an illumination source having a different shape than an illumination shape of an inspection tool for acquiring images of the test reticle or another reticle or wafer.

23. The system of claim 21, wherein the lithography model is calibrated with images rendered from a design database for a calibration reticle.

24. The system of claim 21, wherein the lithography model is calibrated with images acquired from a calibration reticle.

25. The system of claim 21, wherein the lithography model includes a compact resist model.

26. The system of claim 21, wherein the lithography model is applied to the reticle near field, which was recovered for the test reticle, under a plurality of different lithography process conditions, and wherein analyzing the simulated test wafer images includes determining whether the test reticle will likely result in an unstable wafer under the different lithography process conditions by comparing portions of the simulated test images associated with different process conditions and a same reticle area.

\* \* \* \* \*